United States Patent [19]
Henderson et al.

[11] Patent Number: 5,414,270
[45] Date of Patent: May 9, 1995

[54] METHOD AND APPARATUS FOR THE AUTOMATIC INSPECTION OF CIGARETTE RODS FOR SPOTS AND STAINS

[75] Inventors: Calvin W. Henderson; Wallace R. Lassiter; William R. Jarvis, all of Winston-Salem, N.C.

[73] Assignee: R. J. Reynolds Tobacco Company, Winston-Salem, N.C.

[21] Appl. No.: 62,101

[22] Filed: May 14, 1993

[51] Int. Cl.⁶ .......................................... G01N 21/88
[52] U.S. Cl. .................................... 250/572; 209/536
[58] Field of Search ............... 250/571, 572, 562, 563, 250/561; 209/535, 536; 382/8, 34; 356/237; 348/89, 92

[56] References Cited

U.S. PATENT DOCUMENTS

| | | | |
|---|---|---|---|
| 4,639,592 | 1/1987 | Heitmann | 250/572 |
| 4,845,374 | 7/1989 | White et al. | 250/561 |
| 5,235,649 | 8/1993 | Reda | 209/536 |

*Primary Examiner*—David C. Nelms

[57] ABSTRACT

A method of and apparatus for automatically inspecting cigarette rods for spots and stains are disclosed in which a hopper assembly apparatus is utilized to present cigarette samples one at a time to a CCD camera which takes an image of a 36 degree slice of the surface of the outer wrapper of the cigarette. The image is digitized, analyzed and stored. The cigarette is then rotated through 360 degrees and an image of each 36 degree segment of its outer surface is obtained, analyzed and the data stored. The system then selects another cigarette and repeats the inspection and evaluation process.

30 Claims, 4 Drawing Sheets

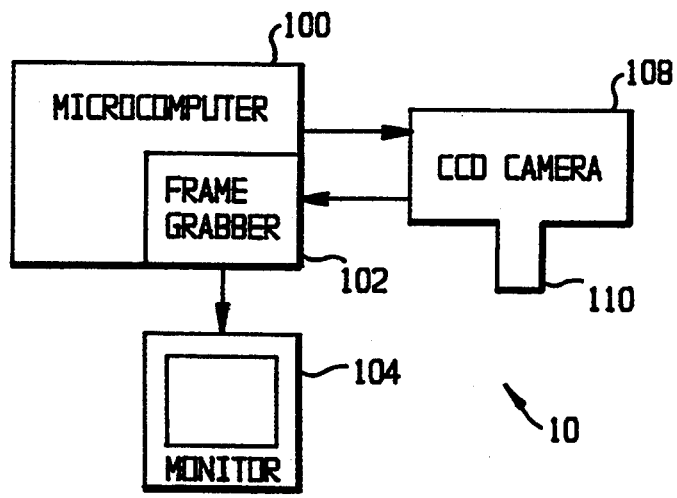
FIG. 1
FIG. 5
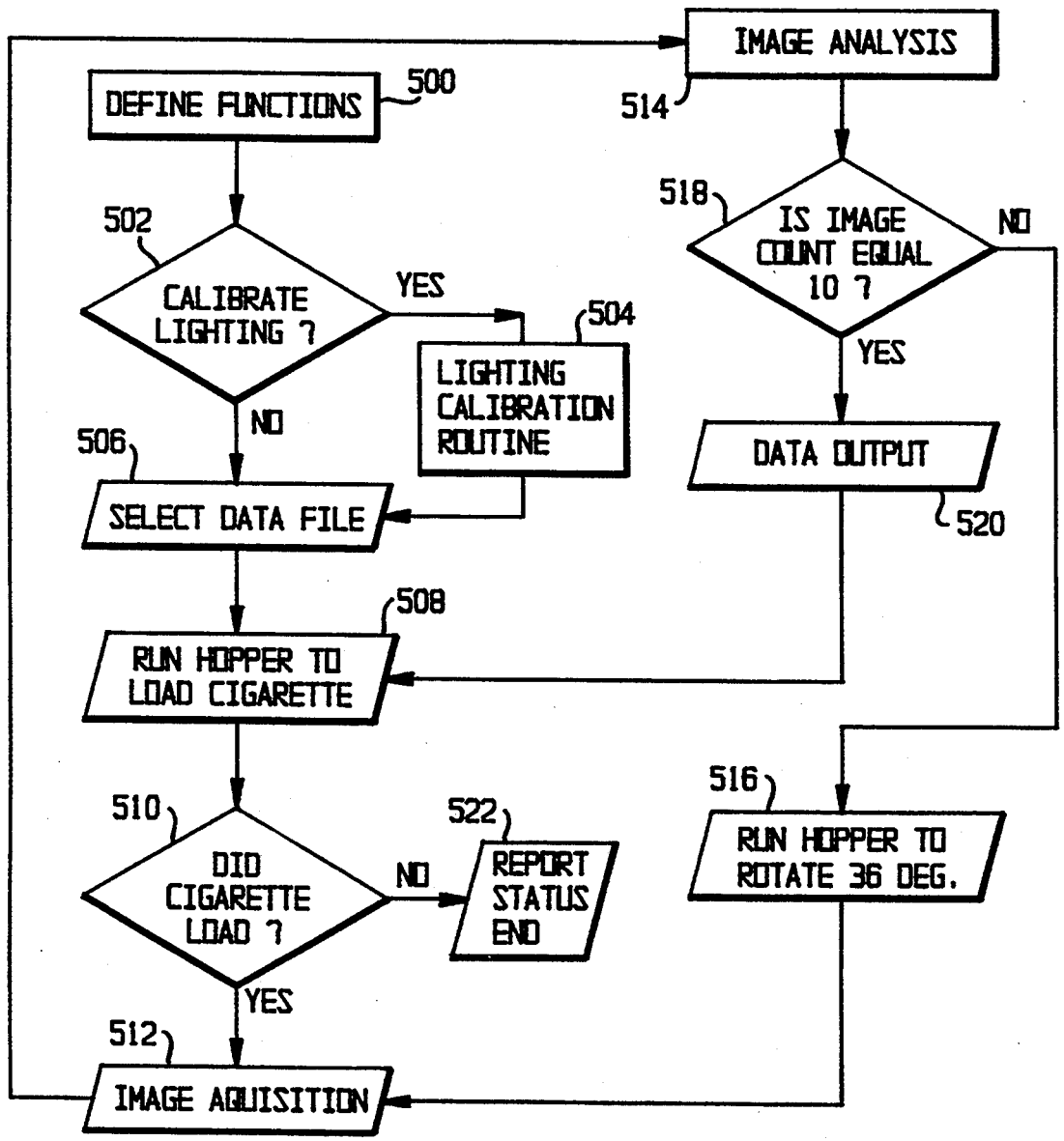

METHOD AND APPARATUS FOR THE AUTOMATIC INSPECTION OF CIGARETTE RODS FOR SPOTS AND STAINS

FIELD OF THE INVENTION

The present invention relates to a method of and apparatus for inspecting finished products and, more particularly, to a method of and apparatus for inspecting the outer casing of cigarette rods for spot and stain defects.

BACKGROUND OF THE INVENTION

During the process of producing cigarettes, cigarette manufacturers strive to manufacture the highest quality of cigarettes possible. Producing a high-quality cigarette includes, in addition to perfectly forming the shape of the cigarette and using good quality tobacco, manufacturing a cigarette in which the outer wrapper of the cigarette, which is typically bright white in color, does not contain any blemishes. Typical blemishes which may be found in the outer wrappers of cigarettes are spots and stains. Spots and stains are typically caused by either defects in the paper wrapper itself or, more usually, by the excessive moisture content of the tobacco. Such excessive moisture content can produce tobacco stains and spots on the outer wrapper of a cigarette.

Spots and stains which appear on a finished cigarette rod are considered to be a quality defect. Therefore, to ensure a high quality product, it is desirable to inspect large numbers of cigarettes from various markets throughout the world on a continuous basis to inspect for spots and stains. In that manner, it is possible to determine the percentage of defective cigarettes and to investigate the cause of the spots and stains which appear on the finished cigarette rods.

Historically, the inspection of finished cigarette rods for spots and stains on a continuing basis has been performed by employees visually inspecting large numbers of cigarettes. Typically, three inspectors grade each of the cigarette rods for defects. However, this subjective method of evaluation is undesirable, both because of the labor intensive nature of the task of actually inspecting large numbers of cigarettes for such defects and because of the perceptual differences between the various cigarette inspectors. In fact, the same inspector may grade a cigarette rod differently on different days. Also, spots and stains may change over time, such as, for example, in humid climates.

Therefore, in order to provide a reliable, objective and consistent basis upon which to grade finished cigarette rods for spots and stains, it would be desirable to develop a method for and apparatus which can automatically inspect cigarette rods for spots and stains and, using an electronic inspection and measurement system, grade the inspected cigarette rods for spots and stains in a consistent manner which can be utilized worldwide to inspect large numbers of cigarettes in various geographic markets. In that manner, the results obtained can be objectively compared.

SUMMARY OF THE INVENTION

The present invention is directed to a method of and apparatus for automatically inspecting a large number of cigarette rods for spot and stain defects and objectively quantifying such defect information so that it can be compared with similar information obtained from inspecting other batches of cigarette rods. Spotting and staining defects are objectively measured by using a CCD video camera connected to a microcomputer-based measurement system.

The sample cigarettes are placed in a hopper which is constructed to select the sample cigarettes one at a time and to present each cigarette to the video camera. The video camera and microcomputer system images the entire outer surface of the cigarette rod, in 36 degree increments. The digital image for each 36 degree arc of the cigarette rod is analyzed for spots and stains based on an objective gray level criteria. The spots are categorized as either dark, medium or light. In addition, the square unit area of each category is recorded.

After the sampling process has been repeated ten times in order to provide complete 360 degree coverage of the outer surface of the cigarette rod being sampled, the stored measurements are then summed in order to provide results for the entire cigarette rod. The next cigarette is then selected from the hopper and the measurement process described above is repeated.

With the foregoing and other objects, advantages and features of the invention that will become hereinafter apparent, the nature of the invention may be more clearly understood by reference to the following detailed description of the invention, the appended claims, and to the several views illustrated in the drawings.

BRIEF DESCRIPTION OF THE DRAWINGS

FIG. 1 is a schematic block diagram of the image processing equipment used in connection with the present invention;

FIG. 5 is a flow chart illustrating the software operating functions of the present invention.

DETAILED DESCRIPTION OF THE INVENTION

Figure 2:
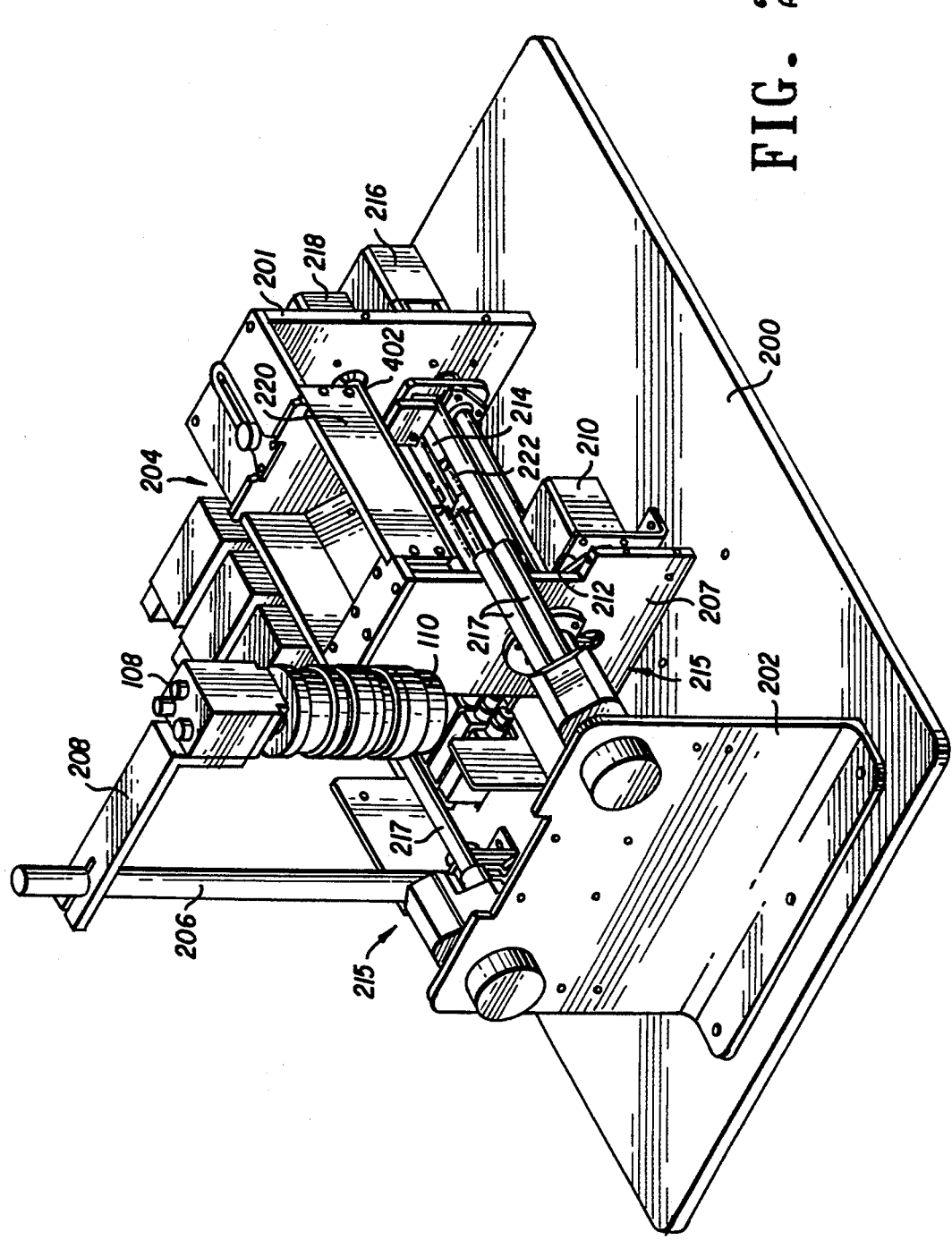
FIG. 2 is a drawing of a front perspective view of the mechanical system of the present invention.

Referring now to the drawings wherein like parts are designated by like reference numerals throughout, there is illustrated in FIG. 1 a schematic block diagram of the image processing equipment 10 used in connection with the present invention. The image processing equipment 10 includes a microcomputer 100 which is connected to control the operation of a CCD camera 108 with a lens 110. The microcomputer 100 may preferably be an IBM or IBM compatible microcomputer of the 486 class, preferably operating at 33 MHz and using VGA graphics. The microcomputer 100 is connected to a standard VGA computer monitor 106.

The microcomputer 100 includes a frame grabber board 102 which is used in conjunction with the CCD camera 108. The frame grabber board 102 is connected to receive the video image signal from the CCD camera 108, a single frame at a time. The video frame grabber board 102 may be obtained from a variety of manufacturers, one such board being Scorpion 16GVGA, manufactured by Univision Technologies, Inc. of Burlington, Mass. The frame grabber board 102 includes a VGA driver so that it directly drives the computer monitor 104. A separate VGA card is not needed for the microcomputer 100. The frame grabber board 102 operates in conjunction with Optimas software available from Bioscan which operates on the microcomputer 100, in order to analyze the digitized video image information produced by the frame grabber 102 from the video image produced by the CCD camera 108. That software, available from Bioscan, Inc., of Edmonds, Wash., is known as the Optimas Image Measurement and Analysis Software.

The CCD camera 108 itself may be Model Number TM-7CN which is a one-half inch CCD camera, available from Pulnix America of Sunnyvale, Calif. The lens 110 used with the CCD camera 108 is preferably a Fujinon 12.5-75 mm manual zoom lens, Model Number H6×12.5R. In the event that a frame grabber board 102 without an on-board VGA driver is used, such a frame grabber board may be connected to a color video monitor (not shown), such as a Sony 13-inch Model PVM-1342Q RGB color video monitor.

Figure 3:
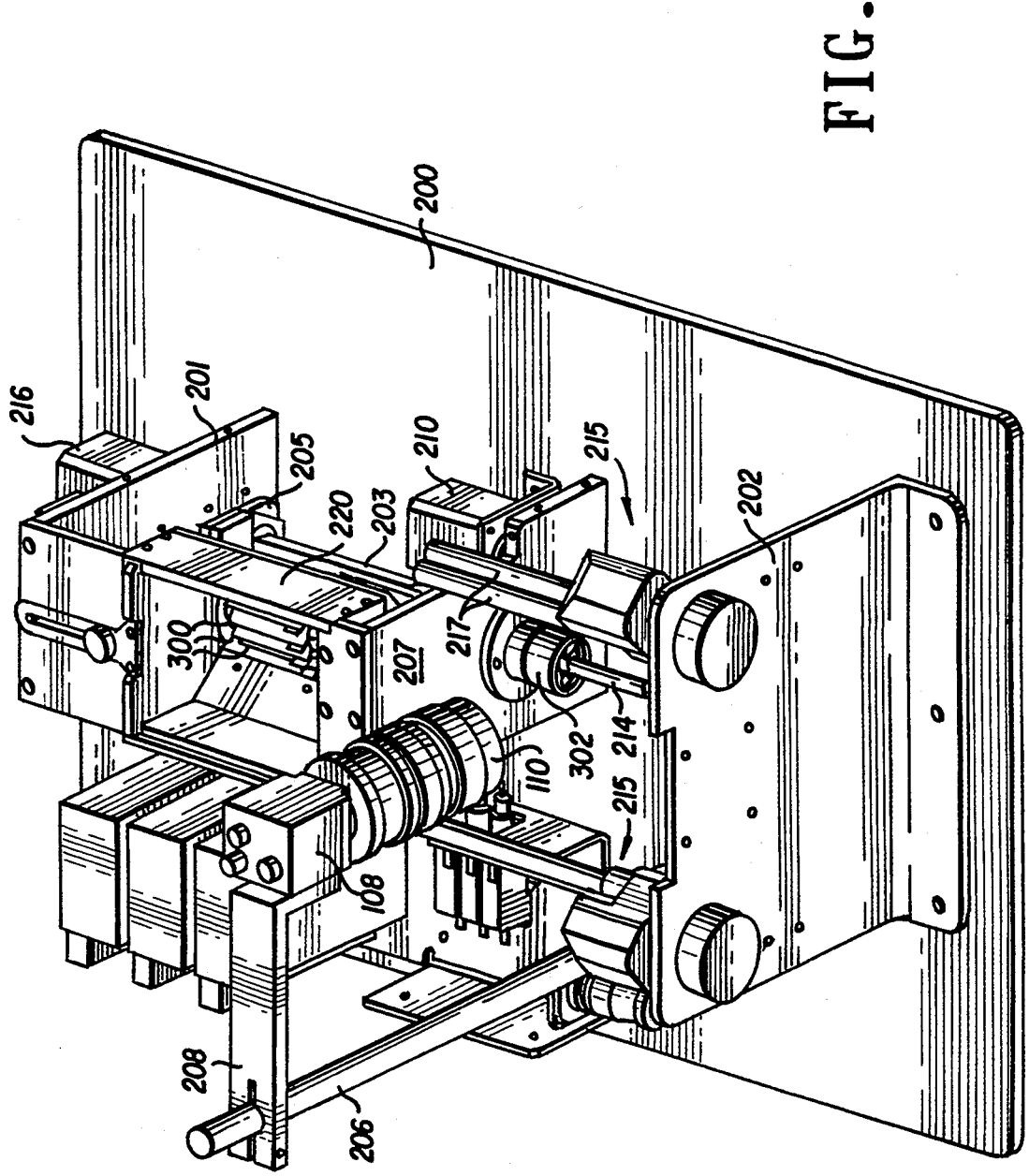
FIG. 3 is a top perspective view of the mechanical system of the present invention shown in FIG. 2.
Figure 4:
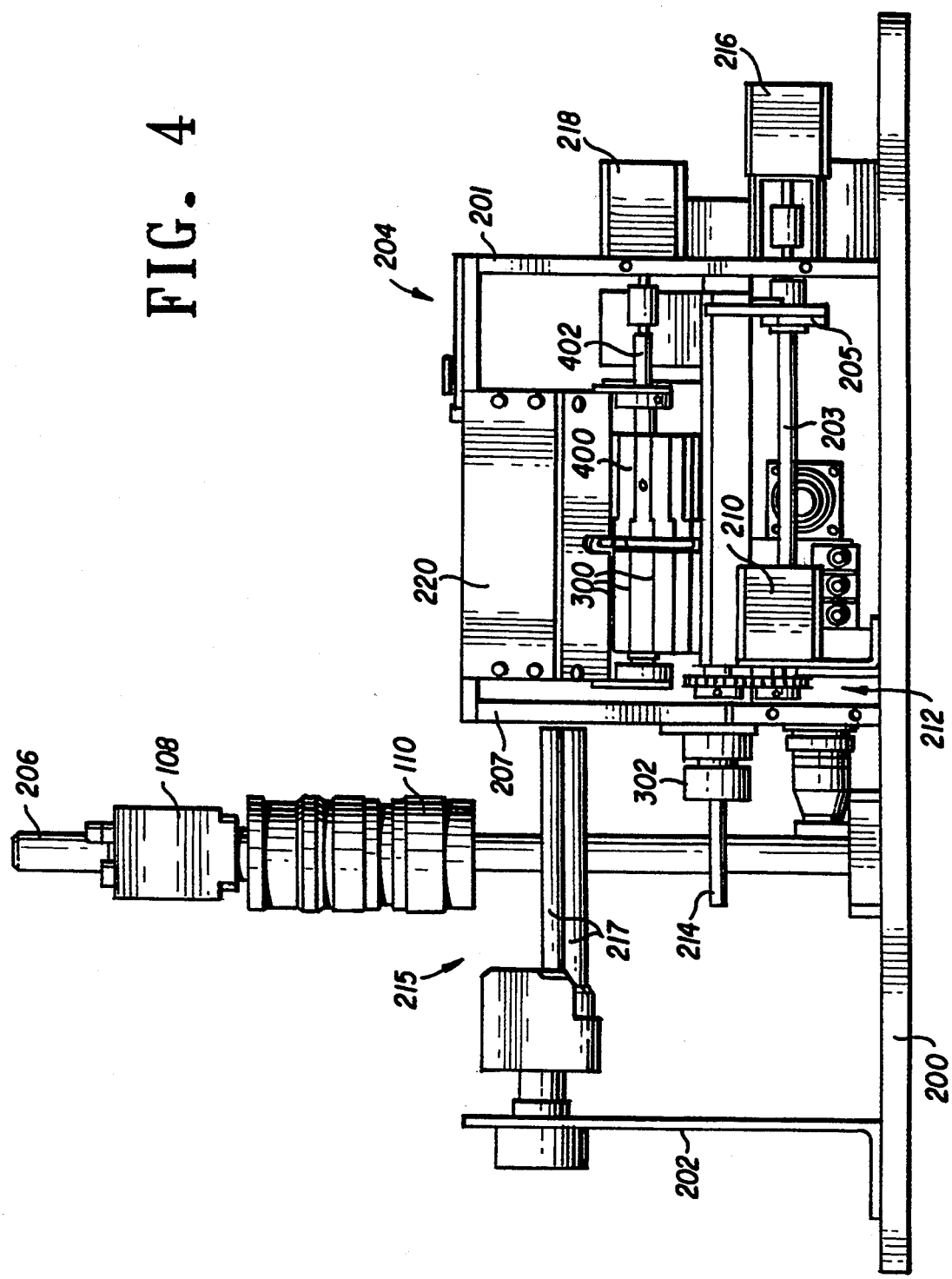
FIG. 4 is a side elevation view of the mechanical system of the present invention.

Referring now to FIGS. 2-4, there is shown the mechanical system of the present invention for storing and handling a number of cigarettes in a hopper assembly 204 and for presenting a single cigarette 214 at a time to the lens 110 of the CCD camera 108. The cigarette storage assembly of the present invention is assembled on a base 200 made from any suitable rigid material, such as aluminum sheet plate. The hopper assembly 204 is secured to the base 200 by suitable means and is used to store the quantity of cigarette samples which is to be inspected and analyzed by the instant invention. Typically, a batch of about 50 sample cigarette rods is loaded into the hopper assembly, inspected and analyzed, although batches of any number of samples could be used.

The hopper assembly 204 includes a motor 218 which is mounted to an end plate 201 of the hopper assembly 204 and drives the hopper drum 400 by means of a suitable connector, such as a drive shaft 402. The hopper drum 400 is constructed with a plurality of fins 300 extending around the circumference of the drum 400. Each of the fins is spaced from the next adjacent fin by a distance sufficient to allow a cigarette to easily rest therebetween.

The hopper drum 400 is situated within the hopper assembly 204 directly beneath the cigarette hopper 220. The cigarette hopper 220 is first filled with cigarettes to be inspected. The hopper drum 400 is then indexed or rotated a predetermined amount, under control of the microcomputer 100. That allows a cigarette to drop between each pair of fins 300 such that, as the drum 400 continues to rotate as indexed, one cigarette 214 is dropped into a channel 222 which extends below the hopper drum 400 and across the entire length of the hopper assembly 204 along an axis parallel to the axis of rotation of the hopper drum 400.

A plunger motor 216 is mounted to end plate 201 of the hopper assembly 204 and is also operated under microcomputer control. When so instructed, motor 216 rotates a threaded shaft 203 which serves to advance a plunger 205 from right to left as viewed in FIG. 4. Plunger 205 pushes a cigarette 214 which has been dropped by the hopper drum 400 into the channel 222 along the length of the channel 222 until the tobacco rod portion of the cigarette 214 exits at the opposite end of the channel 222 through a rotatable cigarette holder 302 (FIGS. 3 and 4). The rotatable cigarette holder 302 may be formed from any suitable construction such that it is able to hold a cigarette in a position approximately parallel to the base 200 and to maintain such parallel relationship during rotation of the cigarette 214 through 360 degrees of rotation. One such construction comprises a plurality of flexible fingers extending radially inwardly from an annular ring or sleeve such that the filter portion is gripped by the finger. About 70 mm of a typical 100 mm filter cigarette preferably protrudes from the rotatable cigarette holder 302 under the camera 108 and lens 110.

The cigarette holder 302 is rotated by a motor 210, using a suitable drive mechanism, such as a belt or chain and pulley arrangement 212. The cigarette holder 302 is rotatably mounted to the end plate 207 of the hopper assembly 204 by means of, e.g., a bearing (not shown), and is aligned with the cigarette channel 222 such that the cigarette to be inspected 214 travels smoothly through the cigarette channel 222 when pushed by the plunger 205 operated by the plunger motor 216 and exits from the end of the cigarette holder 302 for inspection by the CCD camera 108.

The CCD camera 108 and its lens 110 are securely mounted by means of a post 206 and an adjustable mounting plate 208 such that the camera 108 and lens 110 are fixed immediately above the portion of the cigarette 214 which protrudes from the cigarette holder 302. The distance between the camera lens 110 and the cigarette 214 is not critical, however, it should be situated within the focal plane of the lens 110 so that the lens can be properly focused on the exposed surface of the cigarette 214.

The post 206 is secured to the base 200 by any suitable means, such as screws or bolts, such that it extends upwardly from the base 200 in a perpendicular direction. The plate 208 is adjustably secured by suitable means to the post 206 and extends from the post 206 in a plane parallel to the plane of the base 200.

An upstanding plate 202 is mounted to the base 200 and supports a pair of lighting means 215 each comprising a pair of fluorescent light sources 217.

A flow chart of the software which operates on the microcomputer 100 for controlling the automatic inspection device of the present invention is shown in FIG. 5. Once the system operation is initiated, the various functions are defined at step 500. Such functions include the hopper rotation, plunger operation and the cigarette holder rotation. After the functions have been defined at step 500, a determination is made at step 502 of whether the system has been instructed to calibrate the lighting means 215. The lighting calibration is important for two reasons. First, as lighting devices age, a change occurs in the light output of the device. A fluorescent light source is preferably used in connection with the instant invention, since the light produced by a fluorescent lamp is bright white and is uniform across its entire width, with minimum shadows. Also, the light output of a fluorescent lamp does not vary as much, over time, as that of an incandescent lamp. However, other light sources, such as infrared, may also be used. Secondly, in order for results obtained using a multitude of like cigarette inspection devices located throughout the world to be comparable, the lighting sources used in connection with each individual inspection apparatus must be set to the same standards. Also, the day-to-day inspections conducted on the same individual inspection apparatus should likewise be comparable.

If an affirmative determination is made at step 502, then a lighting calibration routine is carried out at step 504. The lighting calibration routine involves the placing of a card having a known light sensitivity on the base 200 of the instant inspection system directly below the camera with no cigarette present in the cigarette holder 302. Such a card may preferably have an optical density of 0.11 on one side and 0.3 on the other side. Alternatively, a gray card, which is available, for example, from Kodak, may be used. That gray card is coated gray on one side and reflects 18% of white light. The other side of the card is coated white and reflects 92% of white light.

Using the values produced by the two sides of the card, the gain of the video amplifier of the CCD camera 108 is first adjusted, and then its offset is adjusted. In that manner, compensation is made for the intensity of the light source in order to produce a consistent readout value from each CCD camera.

Thus, each of the cigarette inspection systems of the present invention can be calibrated to the same lighting standards, no matter the location at which it is used to perform cigarette inspections. The lighting calibration routine is preferably carried out by the microcomputer 100; however, it could also be performed manually. The calibration may preferably be made at the beginning of each batch operation of the cigarette inspection system, or once a day.

After completing the lighting calibration routine 504 or upon a negative determination at step 502, meaning that no calibration routine is to be performed, the software then selects a data file at step 506. A data file contains such information as the number of pixels at each of 256 levels, the number of spots that satisfy a dark spot gray level criteria, the total square unit area of all the dark spots, the number of spots that satisfy a medium spot gray level criteria, the total square unit area of all the medium spots, the number of spots that satisfy a light spot gray level criteria and the total square unit area of all the light spots. Use of such multi-gray scale level criterion is discussed hereinafter.

The hopper assembly 204 is then operated to load a cigarette 214 into position beneath the camera 108 and its lens 110 at step 508, as has previously been described. A determination is then made at step 510 of whether a cigarette has been loaded into the field of view of the CCD camera 108. If it is determined at step 510 that a cigarette has not been loaded into the field of view of the CCD camera 108, then a report status is generated at step 522 on the computer monitor 106, or other appropriate output device connected to the microcomputer 100, and the program ends.

If an affirmative determination is made at step 510 that a cigarette has been loaded into the field of view of the camera, then the CCD camera 108 and lens 110 form and transmit an image of a slice of 36 degrees of the circumference of the cigarette to the frame grabber 102, at the image acquisition step 512. Preferably, each image encompasses 50 mm of the length of the cigarette 214 extending outwardly from the rotatable cigarette holder 302.

Each image is then analyzed at step 514, using the Optimas software. A count of the images is then made at step 518 to determine whether the image count is equal to 10. If a negative determination is made at step 518, meaning that images totalling less than 360 degrees slice of the cigarette have been acquired, then the cigarette holder 302 is rotated another 36 degrees at step 516 and the image of the approximately 36 degrees of the circumference of the cigarette closest to the CCD camera 108 and lens 110 is again acquired at step 512.

If an affirmative determination is made at step 518, meaning that a series of ten images which total 360 degrees of the circumference of the cigarette 214 have been obtained, then the data is output at step 520 for statistical analysis and the program then goes to step 508 to run the hopper assembly 204 to load another cigarette for analysis. After the last cigarette has been loaded and its image acquired, a negative determination is made at step 510, a report status is generated at step 522 and the program then ends.

In operation, the hopper 220 is first loaded with approximately 50 cigarettes which are to be objectively analyzed. The hopper drum 400 is then rotated/indexed by the motor 218 under a command from the microcomputer 100 such that a single sample cigarette is selected by means of the multiple vanes 300 arranged around the circumference of the hopper drum 400. In that manner, a single cigarette is dropped into the cigarette channel 222 where it is pushed, by means of a plunger 205 operated by the motor 216 down the length of the channel 222 until it exits from the cigarette holder 302 such that approximately 70 percent of the length of the cigarette is exposed outside of the cigarette holder 302 in view of the black and white CCD camera 108 and its associated zoom lens 110. Each succeeding cigarette, as it is loaded into the rotatable cigarette holder 302, pushes out the cigarette 214 then held by the cigarette holder 302.

Under control of the microcomputer 100 and its associated software, the CCD camera 108 generates an image of a slice of the cigarette rod 214 which is 36 degrees of the outer surface of that cigarette rod. The image is acquired electronically from the CCD camera 108 and digitized by means of the frame grabber 102.

The digitized image produced by the frame grabber 102 is then analyzed for spots and stains using the Optimas software operating on the microcomputer 100, based preferably on gray level criteria. Based upon such a criteria, for example, the value of 0 would be equal to black whereas a value of 255 would be equal to white. Thus, 256 gray levels are available for ranking the values of spots and stains. The spots are thus characterized depending upon the determined gray level, as either dark, medium or light and the number of each category of such gray levels is counted and stored. In addition, the square unit area of each category of spots on the particular slice of the cigarette rod being analyzed is stored.

Alternatively, the digitized data can be analyzed on an individual gray scale basis by determining and storing the number of occurrences of each gray scale level from 0 to 255. While that technique results in faster data acquisition than the preferred technique, the results must then be analyzed.

After the image is analyzed, the motor 210 is utilized to rotate/index the cigarette holder 302 such that the next 36 degrees of the outer surface of the cigarette rod 214 is exposed to the CCD camera 108 for imaging. This process is repeated ten times in order to provide a complete 360 degree coverage of the outer wrapper of the cigarette rod of the sample being analyzed. The stored measurements for each of the ten segments of the sample cigarette being analyzed are then summed in order to obtain results for the entire sample. The next cigarette is then selected from the hopper 220 and the process described above begins again for that new sample. The system of the present invention continues to analyze each of the cigarettes placed in the hopper 220 until the hopper is empty, at which time the system enters a stand-by mode.

It should be understood that, if desired, a video monitor 104 may be connected to the frame grabber board 102 such that the output of the CCD camera 108 may be viewed by the operator. Also, although not shown in the drawing FIGS. 2-4, the portion of the instant inspection system between the end plate 207 of the hopper assembly 204 which includes the rotatable cigarette holder 302 and the upstanding plate 202 of the lighting system may be enclosed within a cover (not shown) such that only a small amount of ambient light, if any, reaches the cigarette rod 214 being analyzed. In that way, the calibration of the lighting source used to illuminate the cigarette rod for the CCD camera 108 may be more carefully controlled. In the event that such a cover is utilized, such cover would be formed with a slot for inserting the gray card discussed above, which is used in the lighting calibration routine.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed:

1. A method for automatically inspecting the outer wrappers of cigarettes for spot and stain defects comprising the steps of:
    storing a plurality of cigarettes to be inspected;
    providing a CCD camera and associated lens;
    presenting said at least one of said plurality of cigarettes for viewing by said CCD camera by sequentially rotating said at least one of said plurality of cigarettes;
    generating a video signal representative of at least one of said plurality of cigarettes; and
    analyzing said generated video signal to detect said spot and stain defects.

2. The method of claim 1, further including the step of digitizing said video signal prior to performing said analyzing step.

3. The method of claim 2, wherein said analyzing step includes determining the existence of said spots and stains using gray levels.

4. The method of claim 1, further including the steps of providing illumination for said CCD camera and calibrating said CCD camera such that a predetermined signal may be produced with said CCD camera.

5. The method of claim 1, wherein said step of presenting said at least one of said plurality of cigarettes for viewing by said CCD camera includes presenting a portion of the outer wrapper to said CCD camera and then sequentially rotating said at least one of said plurality of cigarettes so that all of said outer wrapper is presented to said CCD camera.

6. The method of claim 3, wherein at least 256 gray levels are used to characterize said video signal.

7. The method of claim 1, wherein said step of analyzing said generated video signal includes the step of determining the area of said outer wrapper covered by said spot and stain defects.

8. The method of claim 3, further including the step of determining the number of pixels of each of said gray levels in order to characterize the spot and stain defects of said at least one of said plurality of cigarettes.

9. The method of claim 3, further including the step of determining the number of each of three gray level scales of said spot and stain defects in order to characterize the spot and stain defects of said at least one of said plurality of cigarettes.

10. The method of claim 1, wherein said step of presenting said at least one of said plurality of cigarettes for viewing by said CCD camera includes presenting a first portion of the outer wrapper to said CCD camera and then sequentially rotating said at least one of said plurality of cigarettes so that at least a second portion of said outer wrapper is presented to said CCD camera.

11. Apparatus for automatically inspecting the outer wrappers of cigarettes for spot and stain defects, comprising:
    means for storing a plurality of cigarettes to be inspected;
    means for generating a video image representative of at least one of said plurality of cigarettes;
    means for presenting at least one of said plurality of cigarettes to said means for generating a video image including means for rotating said at least one of said plurality of cigarettes; and
    means for analyzing said video image to detect said spot and stain defects.

12. The apparatus of claim 11, wherein said means for generating a video image comprises a CCD camera.

13. The apparatus of claim 11, wherein said means for analyzing said video image comprises means for digitizing said video image.

14. The apparatus of claim 11, wherein said means for analyzing said video image further comprises means for characterizing said digitized image according to predetermined gray level values.

15. The apparatus of claim 11, wherein said means for presenting said at least one of said plurality of cigarettes to said means for generating a video image includes means for rotating said at least one of said plurality of cigarettes through 360 degrees of rotation so that the entire circumference of the outer wrapper is presented to the video image generating means.

16. The apparatus of claim 11, further including means for calibrating said means for generating a video image such that a predetermined reference signal may be produced by said means for generating a video image.

17. The apparatus of claim 14, wherein at least 256 predetermined gray level values are used to characterize said video image.

18. The apparatus of claim 11, where said means for analyzing said video image determines the area of said outer wrapper covered by said spot and stain defects.

19. The apparatus of claim 14, wherein a determination of the number of pixels of each of said gray level values is made in order to characterize the spot and stain defects of said at least one of said plurality of cigarettes.

20. The apparatus of claim 14, wherein the number of defects characterized by a predetermined three gray level scale is made in order to characterize the spot and stain defects of said at least one of said plurality of cigarettes.

21. The apparatus of claim 11, wherein said means for presenting said at least one of said plurality of cigarettes to said means for generating a video image includes means for rotating said at least one of said plurality of cigarettes so that at least a portion of the entire circumference of the outer wrapper is presented to the video image generating means.

22. A method for automatically inspecting the outer wrappers of cigarettes for spot and stain defects comprising the steps of:

storing a plurality of cigarettes to be inspected;

providing a CCD camera and associated lens;

presenting said at least one of said plurality of cigarettes for viewing by said CCD camera by rotating said at least one of said plurality of cigarettes;

generating a video signal representative of at least one of said plurality of cigarettes; and analyzing said generated video signal to detect said spot and stain defects.

23. The method of claim 22, further including the step of digitizing said video signal prior to performing said analyzing step.

24. The method of claim 23, wherein said analyzing step includes determining the existence of said spots and stains using gray levels.

25. The method of claim 22, further including the steps of providing illumination for said CCD camera and calibrating said CCD camera such that a predetermined signal may be produced with said CCD camera.

26. The method of claim 22, wherein said step of presenting said at least one of said plurality of cigarettes for viewing by said CCD camera includes presenting a portion of the outer wrapper to said CCD camera and then sequentially rotating said at least one of said plurality of cigarettes so that all of said outer wrapper is presented to said CCD camera.

27. The method of claim 24, wherein at least 256 gray levels are used to characterize said video signal.

28. The method of claim 22, wherein said step of analyzing said generated video signal includes the step of determining the area of said outer wrapper covered by said spot and stain defects.

29. The method of claim 24, further including the step of determining the number of pixels of each of said gray levels in order to characterize the spot and stain defects of said at least one of said plurality of cigarettes.

30. The method of claim 24, further including the step of determining the number of each of three gray level scales of said spot and stain defects in order to characterize the spot and stain defects of said at least one of said plurality of cigarettes.

* * * * *